United States Patent
Jorda et al.

(10) Patent No.: US 8,507,003 B2
(45) Date of Patent: Aug. 13, 2013

(54) COMPRESSED TABLETS COMPRISING MICROCAPSULES WITH MODIFIED RELEASE

(75) Inventors: Rafaël Jorda, Merignac (FR); Pierre Autant, Commentry (FR)

(73) Assignee: Flamel Technologies (FR)

( * ) Notice: Subject to any disclaimer, the term of this patent is extended or adjusted under 35 U.S.C. 154(b) by 1951 days.

(21) Appl. No.: 10/507,886

(22) PCT Filed: Mar. 14, 2003

(86) PCT No.: PCT/FR03/00827
§ 371 (c)(1), (2), (4) Date: Jun. 23, 2005

(87) PCT Pub. No.: WO03/077888
PCT Pub. Date: Sep. 25, 2003

(65) Prior Publication Data
US 2005/0266078 A1   Dec. 1, 2005

(30) Foreign Application Priority Data
Mar. 18, 2002  (FR) ..................... 02 03336

(51) Int. Cl.
*A61K 9/14* (2006.01)
*A61K 9/22* (2006.01)
*A61K 9/16* (2006.01)

(52) U.S. Cl.
USPC ........... 424/489; 424/468; 424/490; 424/478; 424/429

(58) Field of Classification Search
None
See application file for complete search history.

(56) References Cited

U.S. PATENT DOCUMENTS

| | | | |
|---|---|---|---|
| 4,832,967 A * | 5/1989 | Autant et al. ................... | 426/96 |
| 5,464,632 A | 11/1995 | Cousin et al. | |
| 5,576,021 A | 11/1996 | Andoh et al. | |
| 6,022,562 A * | 2/2000 | Autant et al. ................. | 424/489 |
| 6,077,544 A | 6/2000 | Debregeas et al. | |

FOREIGN PATENT DOCUMENTS

| | | |
|---|---|---|
| CN | 1187121 | 7/1998 |
| EP | 0 202 051 A2 | 11/1986 |
| EP | 0 202 051 A3 | 11/1986 |
| EP | 0 207 041 A2 | 12/1986 |
| EP | 0477135 A1 | 3/1992 |
| EP | 0601508 A2 | 6/1994 |
| GB | 1 598 458 | 9/1981 |
| JP | 58073359 | 5/1983 |
| JP | 63039811 | 2/1988 |
| JP | 2053721 | 2/1990 |
| WO | WO 92/01446 | 2/1992 |
| WO | WO 93/01805 | 2/1993 |
| WO | WO 94/09762 | 5/1994 |
| WO | WO 96/11675 | 4/1996 |
| WO | WO 96/39127 | 12/1996 |
| WO | WO 99/26608 | 6/1999 |
| WO | WO 0239984 A2 * | 5/2002 |
| WO | WO 02/072072 A2 | 9/2002 |

OTHER PUBLICATIONS

Nicklasson et al., "Modulation of the tabletting behaviour of microcrystalline cellulose pellets by the incorporation of polyethylene glycol," *European Journal of Pharmaceutical Sciences 9*, 1999, pp. 57-65.

* cited by examiner

*Primary Examiner* — Michael G Hartley
*Assistant Examiner* — Nabila Ebrahim
(74) *Attorney, Agent, or Firm* — Patton Boggs LLP

(57) ABSTRACT

A multi(micro)particulate tablet is provided comprising microparticles which comprise a mechanically non-deformable core of active principle (AP). The tablet is formed from reservoir microcapsules with prolonged release of the AP, which are each made up of a non-deformable core comprising AP and covered with at least one film coating controlling release of the AP in vivo. The microcapsules have a particle size of between 50 and 1000 microns and are coated with at least one outer overcoating envelope comprising at least one deformable organic constituent having a melting point of between 40° C. and 120° C. The envelope allows the prolonged release of the AP in vivo without modification of the release profile when the microcapsules are compressed to form a tablet, even for microparticles not specifically formulated for compression.

29 Claims, 4 Drawing Sheets

COMPRESSED TABLETS COMPRISING MICROCAPSULES WITH MODIFIED RELEASE

This application is the National Stage of International Application No. PCT/FR03/00827, filed Mar. 14, 2003.

The present invention relates to the field of multi(micro)particulate, preferably orally dispersible tablets that make it possible to administer active principles (AP), preferably in high doses.

In particular, the present invention relates to preferably orally dispersible tablets based on microcapsules of the reservoir type that allow the prolonged release of at least one medicinal and/or nutritional active principle (AP) in vivo, these tablet-forming microcapsules being of the type:
  made up of hard cores of AP each covered with at least one film coating controlling the prolonged release of the AP in vivo,
  and having a particle size of between 50 and 1000 microns, preferably of between 100 and 750 microns and particularly preferably of between 200 and 500 microns, and also a specific overcoating.

The invention further relates to these microcapsules that form prolonged-release tablets, said tablets preferably being rapidly orally dispersible and containing high doses of active principle.

Prolonged-release multiparticulate systems for drug administration are well known.

In particular, French patent application FR-A-2 725 623 (FLAMEL TECHNOLOGIES) relates to a multimicroparticulate galenical system for the prolonged release of AP. This system consists of microcapsules for the prolonged oral administration of at least one active principle (excluding acetylsalicylic acid). These microcapsules are made up of a core of active principle covered with a coating based e.g. on ethyl cellulose, polyvinylpyrrolidone, castor oil and magnesium stearate. These microcapsules perform perfectly as regards the prolonged release of the AP in vivo.

However, even though this coating performs its prolonged release function perfectly, it nevertheless remains capable of improvement as regards the compressibility of such microcapsules. In fact, the excipients used in this coating for controlling the prolonged release of the AP are not good at withstanding the mechanical stresses imposed during compression. This results in a degradation of said coating and consequently in a perturbation of its function of controlling the prolonged release of the AP.

The same applies to the invention forming the subject of European patent EP-B-0 548 356, modified in the opposition proceedings, which covers a rapidly disintegrating, multiparticulate tablet comprising an active substance in the form of microcrystals or microgranules provided with a coating, e.g. for masking the taste, and a mixture of excipients devoid of effervescent agents, organic acids and agents that develop a high viscosity in contact with water, said mixture of excipients comprising one or more disintegrating agents such as insoluble crosslinked polyvinylpyrrolidone or carboxymethyl cellulose, and one or more swelling or soluble agents, said swelling agent being such as starch, modified starch or microcrystalline cellulose, said tablet disaggregatinn less than 60 seconds when it is placed in the mouth, without any chewing action, combining with the saliva present to produce a suspension that is easy to swallow.

U.S. Pat. No. 5,464,632, corresponding to EP-B-0 548 356, relates to a tablet capable of rapid disintegration in the buccal cavity without the use of water, said tablet:
  comprising an active substance and a mixture of non-effervescent excipients,
  and affording a reduced influence on the pH in the digestive tract and a reduced influence of the viscosity,
this active substance being multiparticulate in the form of coated microcrystals or microgranules, said mixture of excipients comprising a disintegrating agent and a swelling agent which are responsible for the disintegration of the tablet with the saliva present in the mouth to give, in less than 60 seconds, a suspension that is easy to swallow.

The orally dispersible tablets according to said patents do not offer all the desirable guarantees as regards preservation of the functions of prolonged release of the AP and/or masking of the taste during compression.

This problem of the compressibility of coated microparticles of AP is well known in the prior art. It is referred to particularly in: "International Journal of Pharmaceutics, no. 143, 13-23 (1996)" and in PCT international patent application WO-99/26608. Said documents state that the compression of coated granules modifies the structure of the film coating through cracking or rupture, leading to a partial or total loss of the properties of the film coating. In particular, cracking irreversibly modifies the release profile of the active principle(s) contained in the granules.

The invention described in said patent application WO-99/26608 of the prior art proposes to overcome this problem by providing compressible spheroids containing one or more active principles, except tiagabine, that are directly compressible without the addition of a substantial proportion of an auxiliary substance, namely less than 5% by weight and preferably less than 1% by weight.

These spheroids comprise a core covered with a coating layer. The core and/or the coating layer contain at least one active principle and at least one thermoplastic excipient with a pasty to semisolid consistency at a temperature of 20° C., and a melting point of between 25 and 100° C.

The whole containing the active principle(s) is coated with a deformable flexible film based on a polymeric material with a glass transition temperature below 30° C., which affords either protection, or masking of the taste, or modified and controlled release of the active principle(s).

Example 2 of WO-A-99/26608 involves the preparation of spheroids comprising:
  a neutral core made of sugar;
  a deformable layer of active principle (codeine) combined with the polyethylene glycol PEG 6000, wax, the surfactant TWEEN® 80, dl-α-tocopherol and talcum;
  a deformable coating based on a permeable swelling film based on polyacrylate (Eudragit® NE 30 D) and the polyethylene glycol PEG 6000, Eudragit® NE 30 D being a neutral ester of polyacrylic or polymethacrylic acid;
  and a deformable outer layer comprising OPADRY® II (a combination of polymers and polysaccharides) and the polyethylene glycol PEG 6000.

These spheroids are specifically designed with several soft layers, making them suitable more precisely for producing tablets dispersible in solution, excluding orally dispersible tablets of the type defined in EP-B-0 548 356.

Furthermore, the purpose of the outer layer is so that tablets can be manufactured without the addition of auxiliary substances, and its role is to assure the mutual cohesion of the spheroids, assure the hardness of the tablet and allow it to disaggregate when it is immersed in solution.

These spheroids contain in fine only 8.2% by weight of the AP codeine and can be converted to tablets with a hardness of 20 N.

In addition, it should be noted that the proportions of active principle in the spheroids according to WO-A-99/26608 are extremely limited. This represents a major handicap as regards patient compliance (observance of dosage) when the AP in question have to be in high doses in the tablet obtained from these spheroids. In fact, to achieve the prescribed dose per tablet with small loadings of AP, it is necessary to produce an extremely bulky tablet which elderly and/or weak patients, in particular, have difficulty in swallowing. Under such conditions the success of treatments is quite uncertain.

Finally, the production of tablets without degradation or with minimal degradation of the dissolution of the spheroids requires a specific formulation of said spheroids and their coating, and cannot be envisaged if the microcapsules used do not intrinsically exhibit the requisite flexibility characteristics.

This review of the state of the art shows that it is difficult to find a technical compromise that guarantees both the stability of the release profile of the AP between the "compressed microcapsule" form and the "uncompressed microcapsule" form and maintenance of the mechanical properties of the microcapsules that give them their compressibility. The solutions already proposed involve the construction of microcapsules possessing several deformable layers. This gives rise to difficulties in perfecting the release profile and affords products that are very dilute in terms of active ingredient, i.e. have a low AP content.

Moreover, contrary to current knowledge, a desirable approach to the problem would be to propose a simple technical solution adaptable to any microcapsule or microsphere, rather than integrally to design a microcapsule system.

In such a state of the art, one of the essential objectives of the present invention is to propose a preferably orally dispersible, multi(micro)particulate tablet which comprises one or more active principles capable of being present in high doses, which allows the prolonged release of this (these) active principle(s) in vivo, and whose release profile is not significantly modified by compression, without the microparticles having been specifically formulated for compression as regards the part containing the active principle(s) and the coating agent controlling the dissolution.

Another essential objective of the present invention is to provide a preferably orally dispersible tablet based on microcapsules of the reservoir type which comprises a mechanically non-deformable core of active principle (crystals, granules), which allows the prolonged release of this (these) active principle(s) in vivo, and whose release profile is not significantly modified by compression.

Another essential objective of the present invention is to provide a preferably orally dispersible tablet based on microcapsules of the reservoir type which comprises a hard, i.e. mechanically non-deformable, core of active principle (crystals, granules) and whose release profile is not significantly modified by compression.

Another essential objective of the present invention is to provide a preferably orally dispersible tablet based on microcapsules of the reservoir type which comprises a mechanically non-deformable core of active principle (crystals, granules), which allows the prolonged release of this (these) active principle(s) in vivo, whose release profile is not significantly modified by compression, and which has an appropriate hardness preferably greater than 20 N.

Another essential objective of the present invention is to provide microcapsules of the reservoir type which comprise at least one AP capable of oral administration, and which allow the prolonged release of the AP in vivo, these microcapsules further comprising a mechanically non-deformable core of active principle (crystals, granules) that can be directly compressed without modification of the release profile.

Another essential objective of the present invention is to propose the use of the microcapsules referred to in the above objectives for the preparation of pharmaceutical or dietetic forms (preferably tablets, for example disintegrating or orally dispersible tablets).

These and other objectives are achieved by the present invention, which is based on the principle of dissociating the controlled release function and the compressive strength function within one and the same microcapsule. In other words, it is advantageously proposed according to the invention to use as such, as starting materials, microcapsules developed exclusively for a therapeutic release profile objective, and to coat them with a protective layer for absorbing the mechanical stresses due to the compression operation. This approach addresses the following points:
  possibility of obtaining very specific release profiles,
  optimization of the stability of the microcapsules and maintenance of their properties after compression,
  possibility of administering active principles in high doses.

The present invention therefore relates first and foremost to a preferably orally dispersible tablet based on microcapsules of the reservoir type that allow the prolonged release of at least one medicinal and/or nutritional active principle (AP) in vivo, these tablet-forming microcapsules being of the type:
  each made up of a non-deformable core comprising AP and covered with at least one film coating controlling the prolonged release of the AP in vivo,
  and having a particle size of between 50 and 1000 microns, preferably of between 100 and 750 microns and particularly preferably of between 200 and 500 microns,
characterized in that these microcapsules comprise at least one outer overcoating envelope based on at least one deformable organic constituent having a melting point of between 40° C. and 120° C. and preferably of between 45° C. and 110° C.

Without implying a limitation, the novel prolonged-release galenical system formed by this preferably orally dispersible tablet is particularly advantageous for active principles administered in high doses.

The microcapsules forming the tablet according to the invention provide pharmaceutical formulators in particular with a tool enabling them to produce a tablet containing a single high nyctohemeral dose of any of a large number of AP.

In fact, the overcoating that constitutes one of the essential structural characteristics of the microcapsules used in the tablet of the invention provides mechanical strength during compression without thereby affecting the prolonged release properties conferred by the coating of the core of AP of said microcapsules.

Dissociating the functions of protecting and controlling the release of the AP within different layers of the microcapsules is one of the keys to the stability of said microcapsules on compression.

In terms of the invention:
  The qualifier "non-deformable" or "hard", relating to the particles comprising the AP, refers to the behaviour in a specific compression test Tc whereby the percentage by weight released/dissolved is at least 20% greater for the particles which have undergone the compression test Tc than that observed for the same particles which have not undergone the compression test.
  The test Tc is defined below in the introductory section of the Examples.

The term "orally dispersible" denotes the property of the tablet whereby it is capable of disintegrating rapidly in the mouth, simply with the help of the saliva, to form a suspension that is easy to swallow.

The term "microcapsules" denotes submillimetric film-coated particles of the reservoir type, as opposed to microspheres of the matrix type. These microcapsules can be likened to vehicles that allow the transport and release of one or more AP within the absorption window of the small intestine.

The microcapsules obtained after the film-coating of hard cores are a priori non-deformable (i.e. not resistant to compression). This hardness and the non-deformable character are represented in the compression test Tc by the fact that the amount of AP released at a given time increases substantially after compression of these microcapsules (cf. introduction to the Examples).

According to one preferred characteristic of the invention, the concentration of deformable organic constituent in the overcoating is greater than or equal to 10% by weight and preferably between 20 and 100% by weight.

The outer overcoating envelope belonging to the microcapsules used in the tablet according to the invention derives part of its originality from the fact that it results from a careful choice of deformable constituent from organic compounds having a melting point of between 40 and 120° C., these compounds being selected:

from polymers and copolymers based on alkylene glycols, particular preference being given to polyethylene glycols and especially to polyethylene glycols having a molecular weight of 6000 to 20,000 D, and/or from fats such as hydrogenated vegetable oils, fatty acids, fatty alcohols, fatty acid and/or fatty alcohol esters, polyolefins and mineral, vegetable, animal or synthetic waxes, particular preference being given according to the invention to fatty acid esters such as diglycerides and triglycerides and mixtures thereof, glycerol behenate and hydrogenated oils, hydrogenated castor, soya bean, cottonseed and palm oils.

Said organic overcoating constituent(s) with a melting point advantageously of between 40 and 120° C. can advantageously be used by themselves or in a mixture with one another, and optionally in association with:

a mineral filler, for example silica or titanium dioxide, or an organic filler, for example microcrystalline cellulose, and/or at least one lubricant, for example magnesium stearate or sodium benzoate, and/or at least one hydrophilic polymer such as water-soluble cellulose derivatives like hydroxypropyl cellulose or hydroxypropyl methyl cellulose, synthetic polymers such as polyvinylpyrrolidone or polyvinyl alcohols (PVA), or acrylic and methacrylic derivatives, for example EUDRAGIT®, and/or a surfactant, for example a polyethoxylated Sorbitan® ester.

This plastically deformable overcoating is advantageous in several respects.

Firstly, it is preferably a conventional pharmaceutical excipient or a mixture of such excipients.

The overcoating according to the invention also has the advantage of guarding against any irritation of the mucosae and of being simple and economic to produce.

The microcapsules used in the tablet of the invention are all the more valuable because they are perfectly tolerated by the organism, especially the stomach, and because they can be prepared by methods conventionally employed in the pharmaceutical industry.

According to one preferred characteristic of the invention, the outer overcoating envelope represents from 5 to 50%, preferably from 10 to 30% and particularly preferably in the order of 20% by dry weight, based on the total weight of the microcapsules.

According to one preferred characteristic of the invention, the particles of AP are chosen from mechanically non-deformable, hard cores of AP, these cores preferably being selected from the group comprising crystals and granules.

The qualitative and quantitative composition of the film coating can be especially as follows:

1—at least one film-forming polymer (P1) insoluble in the tract fluids, present in an amount of 50 to 90 and preferably of 50 to 80% by dry weight, based on the total weight of the coating composition, and consisting of at least one water-insoluble cellulose derivative, ethyl cellulose and/or cellulose acetate being particularly preferred;

2—at least one nitrogen-containing polymer (P2) present in an amount of 2 to 25 and preferably of 5 to 15% by dry weight, based on the total weight of the coating composition, and consisting of at least one polyacrylamide and/or poly-N-vinylamide and/or poly-N-vinyllactam, polyacrylamide and/or polyvinylpyrrolidone being particularly preferred;

3—at least one plasticizer present in an amount of 2 to 20 and preferably of 4 to 15% by dry weight, based on the total weight of the coating composition, and consisting of at least one of the following compounds: glycerol esters, phthalates, citrates, sebacates, cetyl alcohol esters, castor oil, salicylic acid and cutin, castor oil being particularly preferred;

4—and at least one surfactant and/or lubricant present in an amount of 2 to 20 and preferably of 4 to 15% by dry weight, based on the total weight of the coating composition, and selected from anionic surfactants, preferably alkali metal or alkaline earth metal salts of fatty acids, stearic and/or oleic acid being preferred, and/or from non-ionic surfactants, preferably polyethoxylated sorbitan esters and/or polyethoxylated castor oil derivatives, and/or from lubricants such as stearates, preferably calcium, magnesium, aluminium or zinc stearate, or stearylfumarate, preferably sodium stearylfumarate, and/or glycerol behenate, it being possible for said agent to comprise only one or a mixture of the above-mentioned products.

In practice, the composition of the film coating of the microcapsules could comprise e.g. from 60 to 80% of ethyl cellulose, from 5 to 10% of polyvinyl-pyrrolidone, from 5 to 10% of castor oil and 2 to 8% of magnesium stearate. Further details on this coating for controlling the prolonged release of the AP may be found by reference to FR-A-2 725 623, the content of which forms an integral part of the present disclosure.

It should be pointed out, however, that the invention can advantageously be carried out using microcapsules of very diverse compositions, and particularly with microcapsules that have not been specifically formulated with a view to their compression, for example in the form of orally dispersible tablets.

In one preferred embodiment of the invention, the microcapsules have the following composition by weight (% by dry weight):

particles based on AP: from 50 to 80 and preferably from 55 to 65, film coating: from 10 to 30 and preferably from 15 to 25, overcoating envelope: from 10 to 30 and preferably from 15 to 25.

In one advantageous variant of the invention, the overcoated microcapsules can comprise the AP in an amount of ≧50% by dry weight, based on their total weight.

By virtue of such loadings of active principle, it is possible to envisage producing tablets which have a convenient size that is easy to swallow and which comprise, in each unit, the high daily dose of AP required for the patient. This greatly facilitates the patient's compliance with the dosage and hence the success of the treatment.

The compressibility characteristic of the overcoated microcapsules according to the invention is all the more valuable because it affords cohesive and non-friable tablets with a hardness D of ≧20 N, for example.

The AP used to prepare the tablets according to the invention can be selected, without implying a limitation, from at least one of the following wide varieties of active substances: antiulcer drugs, antidiabetics, anticoagiilants, antithrombics, hypolipidaemics, antiarrhythmics, vasodilators, antiangina drugs, antihypertensives, vasoprotectors, fertility promoters, labour inducers and inhibitors, contraceptives, antibiotics, antifungals, antivirals, anticancer drugs, anti-inflammatories, analgesics, antiepileptics, antiparkinsonism drugs, neuroleptics, hypnotics, anxiolytics, psychostimulants, antimigraine drugs, antidepressants, antitussives, antihistamines and antiallergics.

The following may be mentioned among the preferred medicinal AP according to the invention: pentoxifylline, prazosin, aciclovir, nifedipine, diltiazem, naproxen, ibuprofen, flurbiprofen, ketoprofen, fenoprofen, indomethacin, diclofenac, fentiazac, oestradiol valerate, metoprolol, sulpiride, captopril, cimetidine, zidovudine, nicardipine, terfenadine, atenolol, salbutamol, carbamazepine, ranitidine, enalapril, simvastatin, fluoxetine, alprazolam, famotidine, ganciclovir, famciclovir, spironolactone, 5-asa, quinidine, perindopril, morphine, pentazocine, paracetarnol, omeprazole, metoclopramide, aspirin, metformin and mixtures thereof.

Other active principles to which the invention relates can be selected from nutritional and/or dietetic supplements and mixtures thereof, for example vitamins, amino acids, antioxidants, trace elements and mixtures thereof.

In general terms, the mechanically deformable overcoating yielding the microcapsules used in the tablet according to the invention is produced by conventional techniques, for example spraying of the constituents of the overcoating in solution, in suspension, in emulsion or in the molten state in film coating apparatuses such as fluidized air beds or film coating turbines, or e.g. by hot mixing of the microparticles with the constituents of the overcoating, taken in pulverulent form, in suitable apparatuses such as spheronizers or kneaders, or e.g. by coacervation and/or phase separation techniques. Some of these techniques are summarized in the article by C. DUVERNEY and J. P. BENOIT in "L'actualité chimique", December 1986.

The overcoated microcapsules forming the tablet according to the invention possess the technical characteristics that allow the release profiles to be maintained after compression, even for high doses of AP. They therefore form per se a subject of the present invention. These overcoated microcapsules are as defined above with reference to the description of the tablet.

The overcoated microcapsules according to the invention, obtained after the coating of hard and non-deformable microparticles as defined in the introductory section of the Examples, are perfectly resistant to compression. This resistance is evident from the compression test Tc performed on overcoated microcapsules of this type, which clearly shows that the amount of AP released at a given time does not change after compression of these microcapsules.

A further subject of the invention is the use of the overcoated microcapsules as defined above for the preparation of pharmaceutical or dietetic forms, preferably tablets that advantageously disintegrate in the mouth (orally dispersible), film-coated tablets, dispersible tablets or effervescent tablets.

Advantageously, the orally dispersible tablets according to the invention have the particular feature that, as the functional excipient in the rapid disintegration of the tablet in the mouth, they comprise only a disintegrating agent to the exclusion of any swelling agent.

Such tablets can be administered orally, preferably by way of a single daily dose.

It should be pointed out that it may be of value to mix at least two different types of AP in one and the same tablet, at least one of said AP being present in the form of overcoated microcapsules according to the invention.

The differences can involve the nature of the active principle and/or the release profile defined by the coating.

The invention will be explained more clearly by means of the Examples below, given solely by way of illustration, which provide a good understanding of the invention and illustrate its variants as well as its various advantages.

EXAMPLES

The Examples which follow are intended to illustrate the invention without implying a limitation.

The dissolution test Tc used to characterize the tablets according to the invention relative to control tablets is defined below.

The prolonged-release (PR) microcapsules, whether or not overcoated according to the invention, are mixed with 70% w/w of a disintegrating agent (Crospovidone®) and the mixture is then tableted with a manual press by applying increasing compression forces. The pressure transmitted to the product via the die is regulated by means of a pneumatic jack that enables the compression force to be adjusted precisely. The dies used are flat with chamfered edges and have a diameter of between 5 and 20 mm, depending on the pressure to be transmitted to the powder. Each mixture is thus subjected to pressures ranging from 6 to 150 MPa. The dissolution profile of the tablets manufactured is checked (European Pharmacopoeia apparatus) and the change in the amount of active principle released after 1 hour of dissolution, as a function of the pressure applied during compression, is compared for the non-overcoated PR microcapsules and those overcoated according to the invention. It should be pointed out that the presence of Crospovidone® in the mixture makes it possible to avoid aggregation of the microcapsules with one another during compression, the consequence of which would be a secondary degradation of the dissolution profile.

Examples 1 and 2 make it possible to demonstrate that the microcapsules which can be used within the framework of the invention are not resistant to compression if they have not been overcoated according to the invention beforehand.

In Examples 3 to 19, prolonged-release (PR) microcapsules not intrinsically resistant to compression are prepared and then converted to tablets, essentially of the orally dispersible type, but also swallowing tablets, in the absence or presence of an overcoating according to the invention. The similarity or degradation of the dissolution profiles is demonstrated by using the method of comparison described in *SUPAC-MR, CMC 8, September* 1997. This is a least squares method of calculation leading to the expression of a similarity factor 12, which makes it possible to demonstrate the identity between the reference profile and test product profile when the value of f2 is more than 50 or their difference when the factor f2 is less than 50.

Examples 3 to 19 demonstrate that particles not intrinsically resistant to compression can be tableted if they have been overcoated according to the invention beforehand.

DESCRIPTION OF THE FIGURES

FIGS. 3 to 7 show the dissolution profiles of the PR microcapsules and the resulting tablets in the presence and absence of the overcoating according to the invention:

Example 1

Granules of aciclovir are prepared by wet granulation in the presence of 3% of Povidone® K30. The grains are graded and then dried in a fluidized air bed. 4500 g of dry granules of aciclovir with a particle size fraction of between 200 and 500 µm are film-coated with a composition according to FR-A-2 725 623 that allows the prolonged release of the active principle and consists of a 73.1/9.86/7.90/7.90 mixture of ethyl cellulose/magnesium stearate/castor oil/PVP in solution in a 60/40 mixture of acetone/isopropyl alcohol.

30% w/w of these PR microcapsules is mixed with 70% w/w of Crospovidone® (Kollidon® CL). The mixture is compressed in a manual press equipped with a die of diameter 10.5 mm and then 6.5 mm by means of a jack developing an adjustable force of between 1500 and 4500 N. This subjects the tablets produced to a pressure of between 18 and 150 MPa.

To preserve the continuity of stress when the die is changed, the weight of the tablet is kept proportional to the square of the diameter of the die.

Tablets are manufactured at different pressures. These different tablets are subjected to the dissolution test and the change in the dissolution rate after 1 hour as a function of the pressure applied during compression is observed. (Dissolution test: Pharm. Eur., paddle mixer, speed 100 rpm, in 1000 ml of buffer of pH 6.8)ww The results recorded are shown in the Table below.

TABLE 1

| Pressure applied (MPa) | % dissolution after 1 h |
|---|---|
| 0 | 11.9 |
| 18.0 | 25.7 |
| 24.4 | 29.5 |
| 32.6 | 28.5 |
| 40.8 | 32.5 |
| 46.9 | 44.2 |
| 49.0 | 41.1 |
| 57.1 | 41.6 |
| 63.9 | 54.5 |
| 85.2 | 50.7 |
| 106.5 | 57.2 |
| 127.8 | 58.9 |
| 149.1 | 60.0 |

It is found that the dissolution rate increases with compression, demonstrating the poor compressive strength of such microcapsules.

Figure 1:
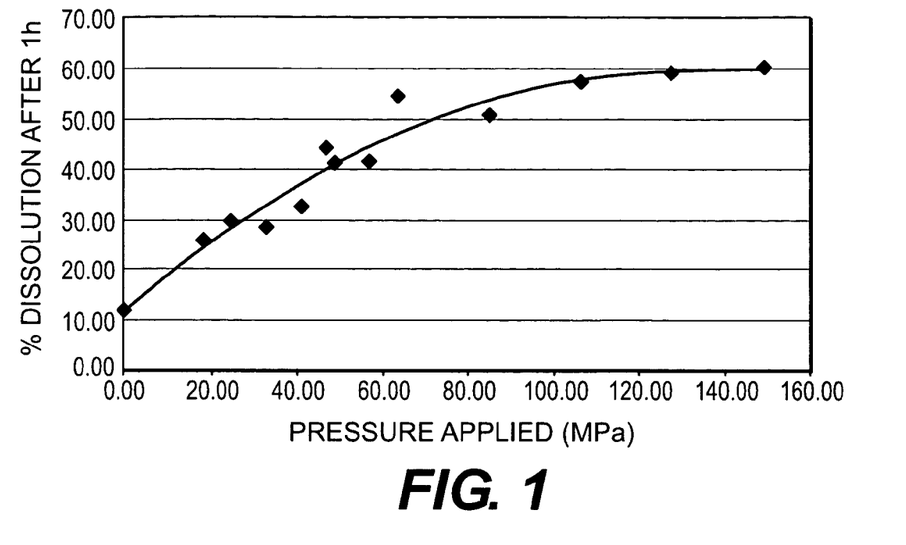
FIG. 1 shows the change in dissolution (release rate of the AP after 1 hour of dissolution) as a function of the pressure exerted on PR microcapsules not overcoated according to the invention (Example 1).

FIG. 1 attached shows the dissolution profile obtained.

Example 2

200 g of the PR coated particles described in Example 1 are overcoated by being film-coated in a fluidized air bed with a mixture composed of 25 g of hydrogenated castor oil (Cutina® HR) and 25 g of polyvinylpyrrolidone (Plasdone® K29-320) in solution in 300 g of isopropyl alcohol. The film coating parameters are as follows:

| | |
|---|---|
| apparatus: | Niro Combi-Coata ® CC1 |
| temperature of film coating solution: | 70° C. |
| flow rate of fluidizing air: | 15 m³/h |
| temperature of product: | 38° C. |
| spraying pressure: | 0.7 bar |
| temperature of spraying air: | 70° C. |
| flow rate of sprayed solution: | 3 g/min |

As in Example 1, these overcoated PR particles are mixed with 70% w/w of Crospovidone® and then compressed at different pressures.

The results recorded are shown in the Table below.

TABLE 2

| Pressure applied (MPa) | % dissolution after 1 h |
|---|---|
| 0 | 11.9 |
| 46.8 | 9.3 |
| 63.9 | 7.7 |
| 85.2 | 9.7 |
| 106.5 | 9.3 |
| 127.8 | 11.2 |
| 149.1 | 11.2 |

Figure 2:
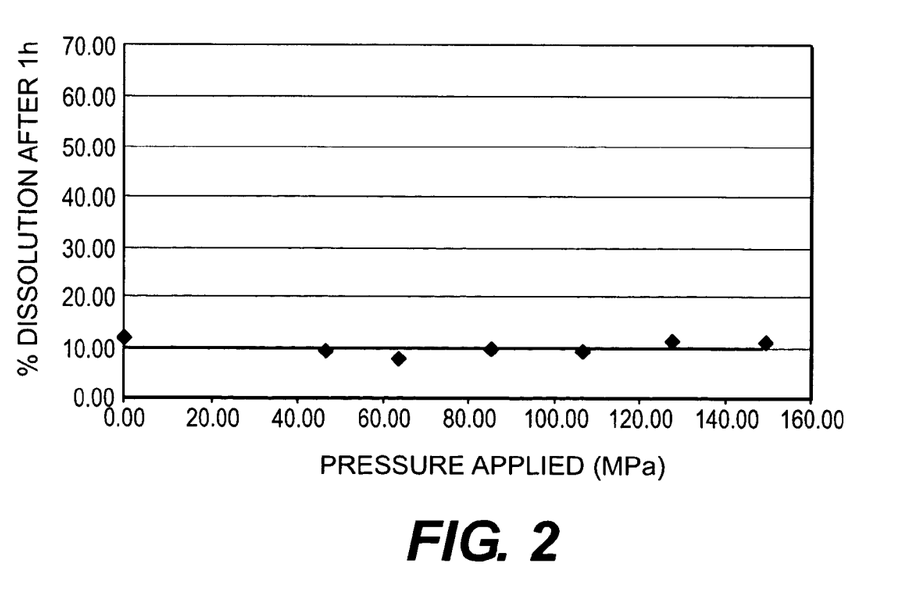
FIG. 2 shows the change in dissolution as a function of the pressure exerted on PR microcapsules previously overcoated according to the invention (Example 2).

FIG. 2 attached shows the dissolution profile obtained.

It is found that the dissolution rate does not increase with compression, demonstrating that microcapsules not intrinsically resistant to compression (cf. Example 1) become resistant when they have been overcoated according to the invention.

Example 3

Manufacture of PR Microcapsules not Intrinsically Possessing a Good Compressive Strength These particles have a core in the form of a hard and brittle monocrystal.

1000 g of crystals of metformin hydrochloride with a particle size of between 200 and 500 microns are film-coated with a composition according to patent FR-A-2 725 623 that allows the prolonged release of the active principle and consists of a mixture of 398.46 g of ethyl cellulose (Ethocel® 7 premium), 43.08 g of polyvinylpyrrolidone (Plasdone® K29-32), 43.08 g of castor oil and 53.85 g of magnesium stearate suspended in a mixture of 3717 g of acetone and 2476 g of isopropyl alcohol.

The coating is effected in a fluidized air bed under the following conditions:

| | |
|---|---|
| apparatus: | Aeromatic ® MP 1 |
| temperature of film coating solution: | room temperature |
| flow rate of fluidizing air: | 65 m³/h |
| temperature of product: | 40° C. |
| spraying pressure: | 2.3 bar |
| temperature of spraying air: | room temperature |
| flow rate of sprayed solution: | 30 g/min |

The dissolution profile, determined by the method of the European Pharmacopoeia with a paddle mixer at 100 rpm in 1000 ml of a buffer of pH 6.8, is as follows:

TABLE 3

| Time (h) | Dissolution (%) |
|---|---|
| 0 | 0 |
| 3 | 41.8 |
| 9 | 81.5 |
| 15 | 93.7 |
| 22 | 98.4 |

Figure 3:
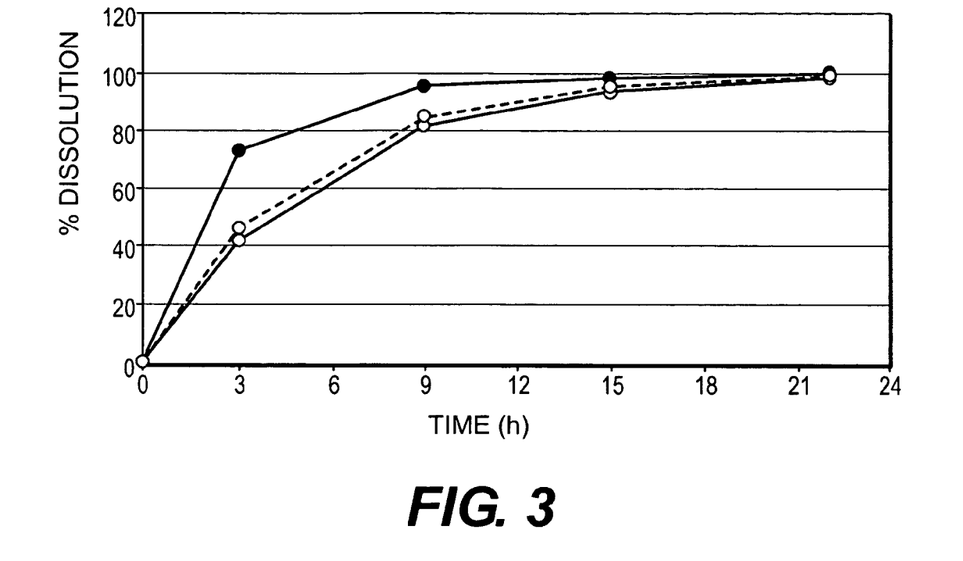
FIG. 3: orally dispersible tablets based on microcapsules of metformin hydrochloride with "slow" prolonged release
-○- microcapsules (Example 3)
-●- tablet of non-overcoated microcapsules (Example 4)
-◯- tablet of overcoated microcapsules (Example 5)

FIG. 3 attached shows the profile obtained.

Example 4

Negative Example Demonstrating Modification of the Dissolution Profile by the Effect of Compression in the Absence of the Overcoating According to the Invention The PR coated particles of Example 3 are converted to orally dispersible tablets using a Korsch alternating press equipped with a flat die of diameter 18 mm, by being mixed with the excipients described below and then directly compressed.
Tablets Containing a 500 mg Dose of Metformin HCl

TABLE 4

| Tablet composition | Unit formulation (mg) |
|---|---|
| PR microcapsules of Example 3 | 769.23 |
| Mannitol (Pearlitol ® 200SD) | 492.31 |

TABLE 4-continued

| Tablet composition | Unit formulation (mg) |
|---|---|
| Crospovidone (Kollidon ® CL) | 230.77 |
| Aspartame ® | 19.23 |
| Flavouring | 16.23 |
| Magnesium stearate | 7.69 |
| Total weight | 1538 mg |
| Hardness | 30N |
| Disaggregation | <60 sec |

The dissolution profile of the tablets obtained, determined under the same conditions as for the initial particles, is as follows:

TABLE 5

| Time (h) | Dissolution (%) |
|---|---|
| 0 | 0 |
| 3 | 72.8 |
| 9 | 95.5 |
| 15 | 98.1 |
| 22 | 99.8 |

FIG. 3 attached shows the profile obtained.

The dissolution similarity test comparing the microcapsules of Example 3 and the tablet of Example 4 yields a coefficient f2 of less than 50. The dissolution profile is modified.

Example 5

Example of Overcoating According to the Invention and Compression of the Overcoated PR Microcapsules 200 g of the PR coated particles obtained in Example 3 are overcoated by being mixed hot (at about 65-70° C.), in a 1 litre reactor equipped with a mechanical stirrer, with a 50 g of polyethylene glycol PEG 6000 introduced in powder form. The mixture is heated to melt the PEG and then gradually cooled, with continuously adapted stirring, until a solid fluid powder is obtained.

After overcoating, the dissolution profile of the microcapsules is as follows:

TABLE 6

| Time (h) | Dissolution (%) |
|---|---|
| 0 | 0 |
| 3 | 36.6 |
| 9 | 80.9 |
| 15 | 94.7 |
| 22 | 99.6 |

These overcoated particles are then converted to orally dispersible tablets using a Korsch alternating press equipped with a flat die of diameter 18 mm, by being mixed with the excipients described below and then directly compressed.
Tablets Containing a 500 mg Dose of Metformin HCl

TABLE 7

| Tablet composition | Unit formulation (mg) |
|---|---|
| PR microcapsules of Example 3 overcoated with PEG | 961.54 |

TABLE 7-continued

| Tablet composition | Unit formulation (mg) |
| --- | --- |
| Mannitol (Pearlitol ® 200SD) | 615.38 |
| Crospovidone (Kollidon ® CL) | 288.46 |
| Aspartame ® | 24.04 |
| Flavouring | 24.04 |
| Magnesium stearate | 9.62 |
| Total weight | 1923 mg |
| Hardness | 30N |
| Disaggregation | <60 sec |

The dissolution profile of the tablets obtained, determined under the same conditions as for the initial particles, is as follows:

TABLE 8

| Time (h) | Dissolution (%) |
| --- | --- |
| 0 | 0 |
| 3 | 46.0 |
| 9 | 84.6 |
| 15 | 95.1 |
| 22 | 98.8 |

FIG. 3 attached shows the dissolution profile obtained for the tablets of overcoated microcapsules.

The dissolution similarity test comparing the microcapsules of Example 3 and the tablet of Example 5 yields a coefficient f2 of more than 50. The dissolution profile is not significantly modified.

Example 6

Manufacture of PR Microcapsules not Intrinsically Possessing a Good Compressive Strength These particles have a core in the form of a hard and brittle monocrystal.

4000 g of crystals of metformin hydrochloride with a particle size of between 200 and 500 microns are film-coated with a composition according to patent FR-A-2 725 623 that allows the prolonged release of the active principle and consists of a mixture of 1040.0 g of ethyl cellulose (Ethocel 7 premium), 112.4 g of polyvinylpyrrolidone (Plasdone K29-32), 112.4 g of castor oil and 140.6 g of magnesium stearate suspended in a mixture of 9700 g of acetone and 6464 g of isopropyl alcohol.

The coating is effected in a fluidized air bed under the following conditions:

| | |
| --- | --- |
| apparatus: | Aeromatic ® MP2 |
| temperature of film coating solution: | room temperature |
| flow rate of fluidizing air: | 250 m³/h |
| temperature of product: | 40° C. |
| spraying pressure: | 2.5 bar |
| temperature of spraying air: | room temperature |
| flow rate of sprayed solution: | 150 g/min |

The dissolution profile, determined by the method of the European Pharmacopoeia with a paddle mixer at 100 rpm in 1000 ml of a buffer of pH 6.8, is as follows:

TABLE 9

| Time (h) | Dissolution (%) |
| --- | --- |
| 0 | 0 |
| 1 | 22.8 |
| 3 | 57.0 |
| 6 | 83.4 |
| 9 | 91.3 |
| 12 | 97.5 |

Figure 4:
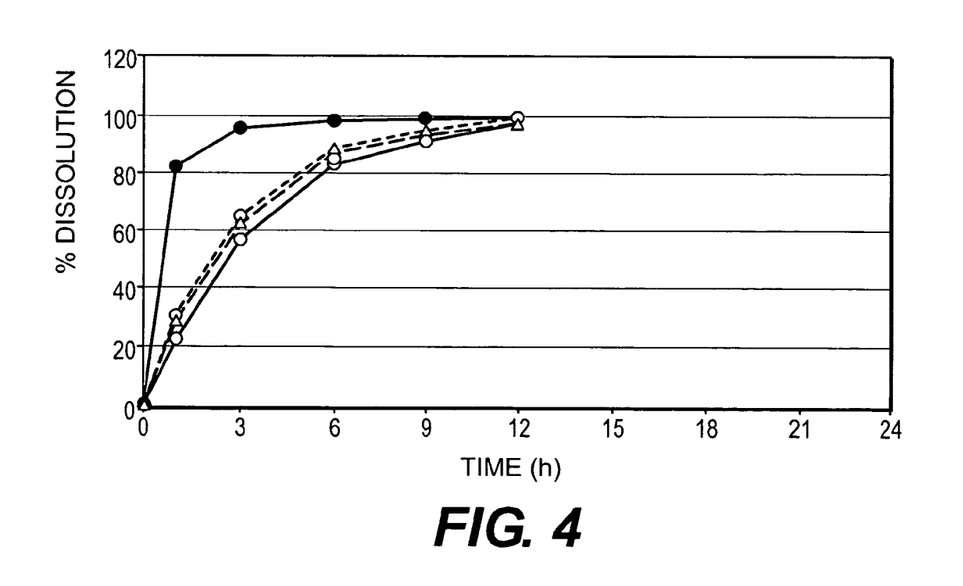
FIG. 4: orally dispersible tablets based on microcapsules of metformin hydrochloride with "rapid" prolonged release
-○- microcapsules (Example 6)
-●- tablet of non-overcoated microcapsules (Example 7)
---○--- tablet of overcoated microcapsules (Example 8)
---◇--- tablet of overcoated microcapsules (Example 9)
---△--- tablet of overcoated microcapsules (Example 10)

FIG. 4 attached shows the dissolution profile obtained.

Example 7

Negative Example Demonstrating Modification of the Dissolution Profile by the Effect of Compression The PR coated particles of Example 6 are converted to orally dispersible tablets using a Korsch alternating press equipped with a flat die of diameter 18 mm, by being mixed with the excipients described below and then directly compressed.

Tablets Containing a 500 mg Dose of Metformin HCl

TABLE 10

| Tablet composition | Unit formulation (mg) |
| --- | --- |
| PR microcapsules of Example 6 | 675.68 |
| Mannitol (Pearlitol ® 200SD) | 432.43 |
| Crospovidone (Kollidon ® CL) | 202.70 |
| Aspartame ® | 16.89 |
| Flavouring | 16.89 |
| Magnesium stearate | 6.76 |
| Total weight | 1351 mg |
| Hardness | 30N |
| Disaggregation | <60 sec |

The dissolution profile of the tablets obtained, determined under the same conditions as for the initial particles, is as follows:

TABLE 11

| Time (h) | Dissolution (%) |
| --- | --- |
| 0 | 0 |
| 1 | 82.4 |
| 3 | 95.7 |
| 6 | 98.6 |
| 9 | 99.2 |
| 12 | 99.4 |

FIG. 4 attached shows the dissolution profile obtained.

The dissolution similarity test comparing the microcapsules of Example 6 and the tablet of Example 7 yields a coefficient f2 of less than 50. The dissolution profile is modified.

Example 8

Example of Overcoating According to the Invention and Compression of the Overcoated PR Microcapsules 200 g of the PR coated particles described in Example 6 are overcoated by being film-coated in a fluidized air bed with a mixture composed of 25 g of hydrogenated castor oil (Cutina® HR) and 25 g of polyvinylpyrrolidone (Plasdone®

K29-320) in solution in 300 g of isopropyl alcohol. The film coating parameters are as follows:

| apparatus: | Niro Combi-Coata ® CC1 |
|---|---|
| temperature of film coating solution: | 70° C. |
| flow rate of fluidizing air: | 15 m³/h |
| temperature of product: | 38° C. |
| spraying pressure: | 0.7 bar |
| temperature of spraying air: | 70° C. |
| flow rate of sprayed solution: | 3 g/min |

The dissolution profile of the overcoated microcapsules is as follows:

TABLE 12

| Time (h) | Dissolution (%) |
|---|---|
| 0 | 0 |
| 1 | 17.4 |
| 3 | 54.5 |
| 6 | 82.1 |
| 9 | 92.6 |
| 12 | 97.6 |

These overcoated particles are converted to orally dispersible tablets using a Korsch alternating press equipped with a flat die of diameter 18 mm, by being mixed with the excipients described below and then directly compressed.

Tablets Containing a 500 mg Dose of Metformin HCl

TABLE 13

| Tablet composition | Unit formulation (mg) |
|---|---|
| PR microcapsules of Example 6 overcoated with hydrogenated castor oil/PVP | 844.59 |
| Mannitol (Pearlitol ® 200SD) | 540.54 |
| Crospovidone (Kollidon ® CL) | 253.38 |
| Aspartame ® | 21.11 |
| Flavouring | 21.11 |
| Magnesium stearate | 8.45 |
| Total weight | 1689 mg |
| Hardness | 30N |
| Disaggregation | <60 sec |

The dissolution profile of the tablets obtained, determined under the same conditions as for the initial particles, is as follows:

TABLE 14

| Time (h) | Dissolution (%) |
|---|---|
| 0 | 0 |
| 1 | 29.8 |
| 3 | 64.8 |
| 6 | 87.0 |
| 9 | 93.1 |
| 12 | 97.3 |

FIG. 4 attached shows the dissolution profile obtained for these tablets of overcoated microcapsules.

The dissolution similarity test comparing the microcapsules of Example 6 and the tablet of Example 8 yields a coefficient f2 of more than 50. The dissolution profile is not significantly modified.

Example 9

Example of Overcoating According to the Invention and Compression of the Overcoated PR Microcapsules 200 g of particles described in Example 6 are overcoated by being film-coated in a fluidized air bed with 25 g of glycerol tripalmitate (Dynasan® 116) and 25 g of polyvinylpyrrolidone (Plasdone® K29-320) in solution in 300 g of isopropyl alcohol. The film coating parameters are identical to those of Example 8.

The dissolution profile of the overcoated microcapsules is as follows:

TABLE 15

| Time (h) | Dissolution (%) |
|---|---|
| 0 | 0 |
| 1 | 19.1 |
| 3 | 55.3 |
| 6 | 82.5 |
| 9 | 92.7 |
| 12 | 97.6 |

These overcoated particles are converted to orally dispersible tablets, containing a 500 mg dose of metformin HCl, by the same method and with the same composition as in Example 8.

The dissolution profile of the tablets obtained, determined under the same conditions as for the initial particles, is as follows:

TABLE 16

| Time (h) | Dissolution (%) |
|---|---|
| 0 | 0 |
| 1 | 31.1 |
| 3 | 65.2 |
| 6 | 87.6 |
| 9 | 93.6 |
| 12 | 99.6 |

FIG. 4 attached shows the dissolution profile obtained for these tablets of overcoated microcapsules.

The dissolution similarity test comparing the microcapsules of Example 6 and the tablet of Example 9 yields a coefficient f2 of more than 50. The dissolution profile is not significantly modified.

Example 10

Example of Overcoating According to the Invention and Compression of the Overcoated PR Microcapsules 200 g of PR coated particles of Example 6 are overcoated in a fluidized air bed with a suspension of 15 g of magnesium stearate in a solution of 35 g of PEG 6000 in 88% isopropyl alcohol.

The film coating conditions are identical to those of Example 8.

The dissolution profile of the overcoated microcapsules is as follows:

TABLE 17

| Time (h) | Dissolution (%) |
|---|---|
| 0 | 0 |
| 1 | 18.4 |
| 3 | 54.8 |
| 6 | 82.2 |
| 9 | 90.3 |
| 12 | 95.5 |

These overcoated particles are converted to orally dispersible tablets, containing a 500 mg dose of metformin HCl, by the same method and with the same composition as in Example 8.

The dissolution profile of the tablets obtained, determined under the same conditions as for the initial particles, is as follows:

TABLE 18

| Time (h) | Dissolution (%) |
|---|---|
| 0 | 0 |
| 1 | 29.5 |
| 3 | 62.8 |
| 6 | 88.9 |
| 9 | 95.0 |
| 12 | 97.6 |

FIG. 4 attached shows the dissolution profile obtained for these tablets of overcoated microcapsules.

The dissolution similarity test comparing the microcapsules of Example 6 and the tablet of Example 10 yields a coefficient f2 of more than 50. The dissolution profile is not significantly modified.

Example 11

Manufacture of PR Microcapsules not Intrinsically Possessing a Good Compressive Strength These particles have a core in the form of a hard and brittle monocrystal.

18,000 g of crystals of acetylsalicylic acid (ASA) with a particle size of between 300 and 500 microns are film-coated with a composition according to patent FR-A-2.704.146 (filing no.: 93 04560) that allows the prolonged release of the active principle and consists of a mixture of 1365.1 g of ethyl cellulose (Ethocel® 7 premium), 77 g of polyvinylpyrrolidone (Plasdone® K29-32), 115.2 g of castor oil, 187.9 g of tartaric acid and 97.9 g of magnesium stearate suspended in a mixture of 15,746 g of acetone and 10,519 g of isopropyl alcohol.

The film coating parameters are as follows:

| | |
|---|---|
| apparatus: | Aeromatic ® MP2 |
| temperature of film coating solution: | room temperature |
| flow rate of fluidizing air: | 350 m³/h |
| temperature of product: | 40° C. |
| spraying pressure: | 3.5 bar |
| temperature of sprayed air: | room temperature |
| flow rate of sprayed solution: | 250 g/min |

The dissolution profile, determined by the method of the European Pharmacopoeia with a paddle mixer at 100 rpm in 1000 ml of a buffer of pH 7.4, is as follows:

TABLE 19

| Time (h) | Dissolution (%) |
|---|---|
| 0 | 0 |
| 3 | 29.8 |
| 9 | 58.1 |
| 15 | 71.8 |
| 22 | 81.5 |

Figure 5:
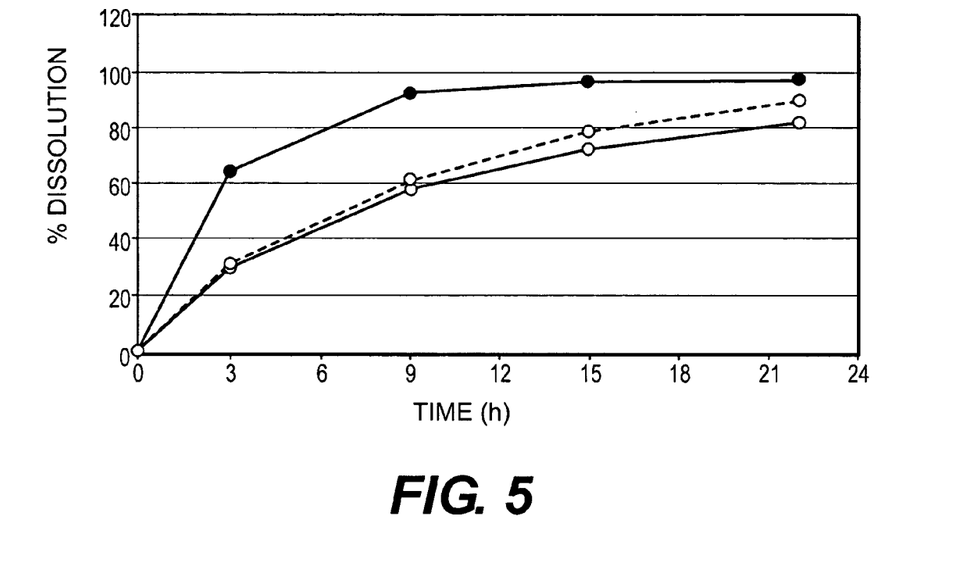
FIG. 5: orally dispersible tablets based on microcapsules of aspirin with prolonged release
-○- microcapsules (Example 11)
-●- tablet of non-overcoated microcapsules (Example 12)
---○--- tablet of overcoated microcapsules (Example 13)

FIG. 5 attached shows the dissolution profile obtained for these tablets of non-overcoated microcapsules.

Example 12

Negative Example Demonstrating Modification of the Dissolution Profile by the Effect of Compression The PR coated particles of Example 11 are converted to orally dispersible tablets using a Korsch alternating press equipped with a flat die of diameter 18 mm, by being mixed with the excipients described below and then directly compressed.

Tablets Containing a 500 mg Dose of ASA

TABLE 20

| Tablet composition | Unit formulation (mg) |
|---|---|
| PR microcapsules of Example 11 | 551.27 |
| Mannitol (Pearlitol ® 200SD) | 352.81 |
| Crospovidone (Kollidon ® CL) | 165.38 |
| Aspartame ® | 13.78 |
| Flavouring | 13.78 |
| Magnesium stearate | 5.51 |
| Total weight | 1102 mg |
| Hardness | 30N |
| Disaggregation | <60 sec |

The dissolution profile of the tablets obtained, determined under the same conditions as for the initial particles, is as follows:

TABLE 21

| Time (h) | Dissolution (%) |
|---|---|
| 0 | 0 |
| 3 | 64.0 |
| 9 | 91.8 |
| 15 | 96.5 |
| 22 | 97.5 |

FIG. 5 attached shows the dissolution profile obtained for this tablet of non-overcoated microcapsules.

The dissolution similarity test comparing the microcapsules of Example 11 and the tablet of Example 12 yields a coefficient f2 of less than 50. The dissolution profile is modified.

Example 13

Example of Overcoating According to the Invention and Compression of the Overcoated PR Microparticles 200 g of the PR coated particles described in Example 11 are overcoated by being film-coated in a fluidized air bed with a mixture composed of 30 g of hydrogenated castor oil (Cutina HR) and 20 g of polyvinylpyrrolidone (Plasdone K29-320) in solution in 300 g of isopropyl alcohol.

The film coating parameters are identical to those of Example 8.

The dissolution profile of the overcoated microcapsules is as follows:

TABLE 22

| Time (h) | Dissolution (%) |
|---|---|
| 0 | 0 |
| 3 | 23.5 |
| 9 | 59.2 |
| 15 | 75.3 |
| 22 | 85.5 |

These overcoated particles are converted to orally dispersible tablets using a Korsch alternating press equipped with a flat die of diameter 18 mm, by being mixed with the excipients described below and then directly compressed.

Tablets Containing a 500 mg Dose of ASA

TABLE 23

| Tablet composition | Unit formulation (mg) |
|---|---|
| PR microcapsules of Example 11 overcoated with hydrogenated castor oil/PVP | 689.08 |
| Mannitol (Pearlitol ® 200SD) | 441.01 |
| Crospovidone (Kollidon ® CL) | 206.73 |
| Aspartame ® | 17.23 |
| Flavouring | 17.23 |
| Magnesium stearate | 6.89 |
| Total weight | 1378 mg |
| Hardness | 30N |
| Disaggregation | <60 sec |

The dissolution profile of the tablets obtained, determined under the same conditions as for the initial particles, is as follows:

TABLE 24

| Time (h) | Dissolution (%) |
|---|---|
| 0 | 0 |
| 3 | 30.6 |
| 9 | 61.2 |
| 15 | 78.4 |
| 22 | 89.5 |

FIG. 5 attached shows the dissolution profile obtained for this tablet of overcoated microcapsules.

The dissolution similarity test comparing the microcapsules of Example 11 and the tablet of Example 13 yields a coefficient f2 of more than 50. The dissolution profile is not significantly modified.

Example 14

Negative Example Demonstrating Modification of the Dissolution Profile by the Effect of Compression for Swallowing Tablets The PR coated particles of Example 6 are converted to swallowing tablets using a Korsch alternating press equipped with an oblong die of 19×9.5 mm, by being mixed with the excipients described below and then directly compressed.

Tablets Containing a 500 mg Dose of Metformin HCl

TABLE 25

| Tablet composition | Unit formulation (mg) |
|---|---|
| Microcapsules of Example 6 | 675.68 |
| Microcrystalline cellulose PH102 | 165.73 |
| Glycerol behenate | 8.50 |
| Total weight | 850 mg |
| Hardness | 60N |
| Disaggregation | about 5 min |

The dissolution profile of the tablets obtained, determined under the same conditions as for the initial particles, is as follows:

TABLE 26

| Time (h) | Dissolution (%) |
|---|---|
| 0 | 0 |
| 1 | 98.5 |
| 3 | 102.3 |
| 6 | 102.6 |
| 9 | 102.5 |
| 12 | 102.7 |

Figure 6:
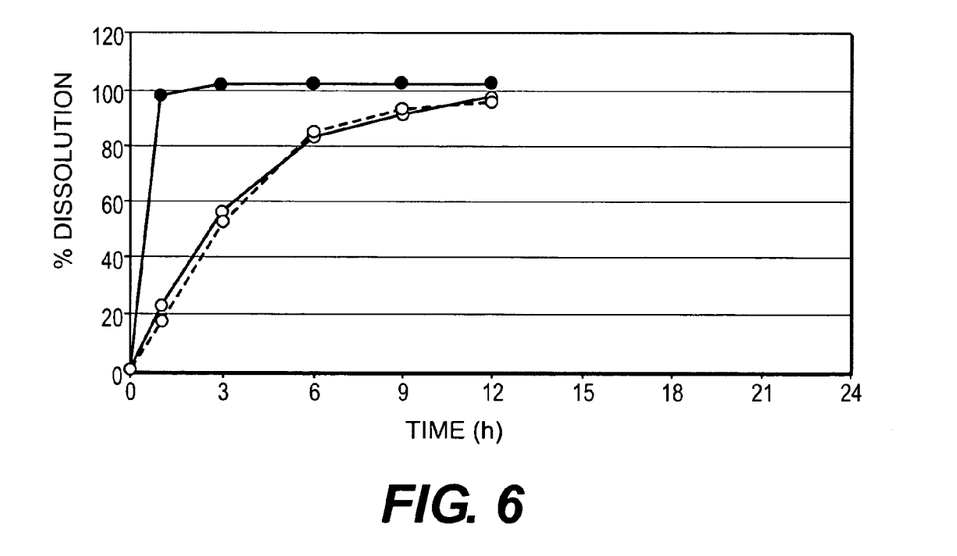
FIG. 6: swallowing tablets based on microcapsules of metformin hydrochloride with prolonged release
-○- microcapsules (Example 6)
-●- tablet of non-overcoated microcapsules (Example 14)
---○--- tablet of overcoated microcapsules (Example 15)

FIG. 6 attached shows the dissolution profile obtained for these tablets of non-overcoated microcapsules.

The dissolution similarity test comparing the microcapsules of Example 6 and the tablet of Example 14 yields a coefficient f2 of less than 50. The dissolution profile is modified.

Example 15

Example of Compression of PR Microcapsules Overcoated According to the Invention Overcoated particles described in Example 9 are converted to swallowing tablets using a Korsch alternating press equipped with an oblong die of 19×9.5 mm, by being mixed with the excipients described below and then directly compressed.

Tablets Containing a 500 mg Dose of Metformin HCl

TABLE 27

| Tablet composition | Unit formulation (mg) |
|---|---|
| Microcapsules of Example 9 overcoated with Dynasan ® /PVP | 844.59 |
| Microcrystalline cellulose PH102 | 207.16 |
| Glycerol behenate | 10.62 |
| Total weight | 1062 mg |
| Hardness | 60N |
| Disaggregation | about 5 min |

The dissolution profile of the tablets obtained, determined under the same condition as for the initial particles, is as follows:

TABLE 28

| Time (h) | Dissolution (%) |
|---|---|
| 0 | 0 |
| 1 | 18.0 |
| 3 | 53.3 |

TABLE 28-continued

| Time (h) | Dissolution (%) |
|---|---|
| 6 | 84.7 |
| 9 | 92.7 |
| 12 | 96.0 |

FIG. 6 attached shows the dissolution profile obtained for these tablets of overcoated microcapsules.

The dissolution similarity test comparing the microcapsules of Example 6 and the tablet of Example 15 yields a coefficient f2 of more than 50. The dissolution profile is not significantly modified.

Example 16

Manufacture of PR Microcapsules not Intrinsically Possessing a Good Compressive Strength These particles have a core in the form of a hard and brittle granule of AP.

Granules of aciclovir are prepared by wet granulation in a Fielder® PMA 65 granulator. For this purpose 11,640 g of finely powdered aciclovir are mixed with 360 g of polyvinylpyrrolidone K30 and then granulated with purified water to give grains. The wet granules are dried in a fluidized air bed and sieved.

4500 g of these sieved granules of aciclovir with a particle size of between 200 and 500 microns are film-coated in a fluidized air bed with a 73.1/9.86/7.90/7.90 mixture of ethyl cellulose/magnesium stearate/castor oil/PVP in solution in a 60/40 mixture of acetone/isopropyl alcohol.

The film coating parameters are as follows:

| | |
|---|---|
| apparatus: | Aeromatic ® MP2 |
| temperature of film coating solution: | room temperature |
| flow rate of fluidizing air: | 200 m³/h |
| temperature of product: | 40° C. |
| spraying pressure: | 2 bar |
| temperature of spraying air: | room temperature |
| flow rate of sprayed solution: | 100 g/min |

The dissolution profile is as follows:

TABLE 29

| Time (h) | Dissolution (%) |
|---|---|
| 0 | 0 |
| 1 | 14.7 |
| 3 | 33.7 |
| 9 | 61.2 |
| 15 | 73.4 |
| 22 | 80.7 |

Figure 7:
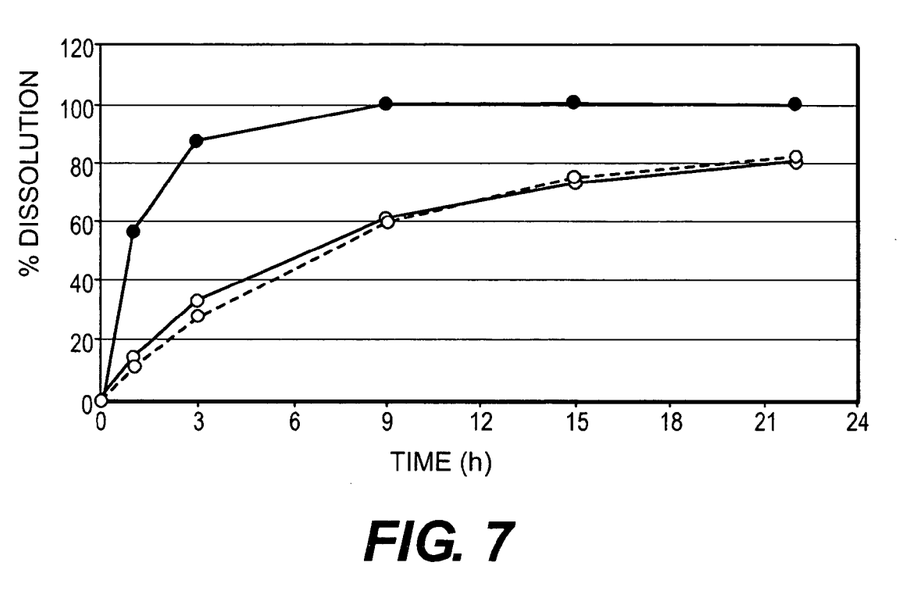
FIG. 7: orally dispersible tablets based on microcapsules of aciclovir with prolonged release
-○- microcapsules (Example 16)
-●- tablet of non-overcoated microcapsules (Example 17)
---○--- tablet of overcoated microcapsules (Example 18)

FIG. 7 attached shows the dissolution profile obtained for the non-overcoated microcapsules.

Example 17

Negative Example Demonstrating Modification of the Dissolution Profile by the Effect of Compression in the Absence of the Overcoating According to the Invention The PR coated particles of Example 16 are converted to orally dispersible tablets using a Korsch alternating press equipped with a flat die of diameter 18 mm, by being mixed with the excipients described below and then directly compressed.

Tablets Containing a 500 mg dose of Aciclovir

TABLE 30

| Tablet composition | Unit formulation (mg) |
|---|---|
| PR microcapsules of Example 16 | 571.43 |
| Mannitol (Pearlitol ® 200SD) | 367.71 |
| Crospovidone (Kollidon ® CL) | 171.43 |
| Aspartame ® | 14.29 |
| Flavouring | 14.29 |
| Magnesium stearate | 5.71 |
| Total weight | 1142.86 mg |
| Hardness | 30N |
| Disaggregation | <60 sec |

The dissolution profile of the tablets obtained, determined under the same conditions as for the initial particles, is as follows:

TABLE 31

| Time (h) | Dissolution (%) |
|---|---|
| 0 | 0 |
| 1 | 57.0 |
| 3 | 87.5 |
| 9 | 100.0 |
| 15 | 101.0 |
| 22 | 100.5 |

FIG. 7 attached shows the dissolution profile obtained for these tablets of non-overcoated microcapsules.

The dissolution similarity test comparing the microcapsules of Example 16 and the tablet of Example 17 yields a coefficient f2 of less than 50. The dissolution profile is modified.

Example 18

Example of Overcoating According to the Invention and Compression of the Overcoated PR Microcapsules 200 g of the PR coated particles described in Example 16 are overcoated by being film-coated in a fluidized air bed with a mixture composed of 25 g of hydrogenated castor oil (Cutina® HR) and 25 g of polyvinylpyrrolidone (Plasdone® K29-320) in solution in 300 g of isopropyl alcohol.

The film coating parameters are identical to those of Example 8.

The dissolution profile of the overcoated microcapsules is as follows:

TABLE 32

| Time (h) | Dissolution (%) |
|---|---|
| 0 | 0 |
| 1 | 9.3 |
| 3 | 26.2 |
| 9 | 55.0 |
| 15 | 68.6 |
| 22 | 76.0 |

These overcoated particles are converted to orally dispersible tablets using a Korsch alternating press equipped with a flat die of diameter 18 mm, by being mixed with the excipients described below and then directly compressed.

Tablets Containing a 500 mg Dose of Aciclovir

TABLE 33

| Tablet composition | Unit formulation (mg) |
|---|---|
| PR microcapsules of Example 16 overcoated with hydrogenated castor oil/PVP | 714.29 |
| Mannitol (Pearlitol ® 200SD) | 457.14 |
| Crospovidone (Kollidon ® CL) | 214.29 |
| Aspartame ® | 17.86 |
| Flavouring | 17.86 |
| Magnesium stearate | 7.14 |
| Total weight | 1428.57 mg |
| Hardness | 30N |
| Disaggregation | <60 sec |

The dissolution profile of the tablets obtained, determined under the same conditions as for the initial particles, is as follows:

TABLE 34

| Time (h) | Dissolution (%) |
|---|---|
| 0 | 0 |
| 1 | 11.4 |
| 3 | 28.4 |
| 9 | 60.2 |
| 15 | 75.0 |
| 22 | 82.0 |

FIG. 7 attached show the dissolution profile obtained for the overcoated microcapsules.

The dissolution similarity test comparing the microcapsules of Example 16 and the tablet of Example 18 yields a coefficient f2 of more than 50. The dissolution profile is not significantly modified.

The invention claimed is:

1. A microcapsule providing prolonged release in vivo of at least one active principle (AP),
    wherein the microcapsule has a particle size of between 50 and 1000 microns;
    wherein the microcapsule comprises a non-deformable core comprising at least one AP in an amount of 50 to 80% by dry weight;
    wherein the non-deformable core is covered with at least one film coating controlling the prolonged release of the AP in vivo;
    and wherein the microcapsule comprises at least one outer overcoating envelope the overcoating envelope consisting of: (1) magnesium stearate and (2) at least 10% by weight of one deformable organic constituent having a melting point of between 40° C. and 120° C., the deformable organic constituent consisting of polyethylene glycol having a molecular weight of between 6,000 and 20,000 D.

2. A method for preparing the microcapsule of claim 1, comprising coating a non-deformable core with at least one outer film overcoating envelope to prepare overcoated microcapsules having a particle size of between 50 and 1000 microns; wherein the microcapsule comprises a non-deformable core comprising at least one AP in an amount of 50 to 80% by dry weight;
    covering the non-deformable core with at least one film coating controlling the prolonged release of the AP in vivo;
    and preparing the overcoating envelope consisting of: (1) magnesium stearate and (2) at least 10% by weight of one deformable organic constituent having a melting point of between 40° C. and 120° C.; wherein the deformable organic constituent consisting of polyethylene glycol having a molecular weight of between 6,000 and 20,000 D.

3. The microcapsule according to claim 1, wherein the at least one film coating comprises at least one film-forming polymer (P1) comprising a water-insoluble cellulose derivative, wherein P1 is insoluble in the tract fluids and present in an amount of 50 to 90% by dry weight, based on the total weight of the coating composition.

4. The microcapsule according to claim 3, wherein P1 is present in an amount of 50 to 80% by dry weight of the coating composition.

5. The microcapsule according to claim 3, wherein P1 is ethylcellulose, cellulose acetate, or a mixtures thereof.

6. The microcapsule according to claim 1, wherein the at least one film coating further comprises at least one nitrogen-containing polymer (P2) comprising polyacrylamide, poly-N-vinylamide, poly-N-vinyllactam, or mixtures thereof, wherein P2 is present in an amount of 2 to 25% by dry weight, based on the total weight of the coating composition.

7. The microcapsule according to claim 6, wherein P2 is present in an amount of 5 to 15% by dry weight of the coating composition.

8. The microcapsule according to claim 6, wherein P2 is polyacrylamide, polyvinylpyrrolidone, or mixtures thereof.

9. The microcapsule according to claim 1, wherein the at least one film coating further comprises at least one plasticizer comprising a glycerol ester, a phthalate, a citrate, a sebacate, a cetyl alcohol ester, castor oil, salicylic acid, cutin, or mixtures thereof, wherein the plasticizer is present in an amount of 2 to 20% by dry weight, based on the total weight of the coating composition.

10. The microcapsule according to claim 9, wherein the plasticizer is present in an amount of 4 to 15% by dry weight of the coating composition.

11. The microcapsule according to claim 9, wherein the plasticizer is castor oil.

12. The microcapsule according to claim 1, wherein the at least one film coating further comprises at least one anionic surfactant, non-ionic surfactant, lubricant, or mixtures thereof present in an amount of 2 to 20% by dry weight, based on the total weight of the coating composition.

13. The microcapsule according to claim 12, wherein the at least one anionic surfactant, non-ionic surfactant, lubricant, or mixtures thereof is present in an amount of 4 to 15% by dry weight of the coating composition.

14. The microcapsule according to claim 12, wherein the anionic surfactant is an alkali metal salt of a fatty acid or an alkaline earth metal salt of a fatty acid; the non-ionic surfactant is a polyethoxylated sorbitan ester, a polyethoxylated castor oil derivative, or mixtures thereof; and the lubricant is calcium stearate, magnesium stearate, aluminium stearate, zinc stearate, a stearylfumarate, glycerol behenate, or mixtures thereof.

15. The microcapsule according to claim 1, wherein the film coating of the microcapsules comprises from 60 to 80% of ethyl cellulose, from 5 to 10% of polyvinylpyrrolidone, from 5 to 10% of castor oil and 2 to 8% of magnesium stearate.

16. The microcapsule according to claim 1, wherein the microcapsules have the following composition by weight: core comprising the AP: from 50 to 80% by dry weight, film coating: from 10 to 30% by dry weight, and overcoating envelope: from 10 to 30% by dry weight.

17. The microcapsule according to claim 1, wherein the microcapsules have the following composition by weight: core comprising the AP: from 55 to 65% by dry weight, film coating: from 15 to 25% by dry weight, and overcoating envelope: from 15 to 25% by dry weight.

18. The microcapsule according to claim 1, wherein the overcoated microcapsules comprise the AP in an amount greater than or equal to 50% of their total dry weight.

19. The microcapsule according to claim 1, wherein the AP is an antiulcer drug, antidiabetic, anticoagulant, antithrombic, hypolipidaemic, antiarrhythmic, vasodilator, antiangina drug, antihypertensive, vasoprotector, fertility promoter, labor inducer, labour inhibitor, contraceptive, antibiotic, antifungal, antiviral, anticancer drug, anti-inflammatory, analgesic, antiepileptic, antiparkinsonism drug, neuroleptic, hypnotic, anxiolytic, psychostimulant, anti-migraine drug, antidepressant, antitussive, antihistamine, or antiallergic.

20. The microcapsule according to claim 1, wherein the AP is pentoxifylline, prazosin, aciclovir, nifedipine, diltiazem, naproxen, ibuprofen, flurbiprofen, ketoprofen, fenoprofen, indomethacin, diclofenac, fentiazac, oestradiol valerate, metoprolol, sulpiride, captopril, cimetidine, zidovudine, nicardipine, terfenadine, atenolol, salbutamol, carbamazepine, ranitidine, enalapril, simvastatin, fluoxetine, alprazolam, famotidine, ganciclovir, famciclovir, spironolactone, 5-asa, quinidine, perindopril, morphine, pentazocine, paracetamol, aspirin, metformin, omeprazole, metoclopramide, or mixtures thereof.

21. The microcapsule according to claim 1, wherein the AP is a nutritional supplement, dietetic supplement, or mixtures thereof.

22. The microcapsule according to claim 1, wherein the AP is a vitamin, amino acid, trace element, antioxidant, or mixtures thereof.

23. The microcapsule according to claim 1, wherein the microcapsules have a particle size of between 100 and 750 microns.

24. The microcapsule according to claim 1, wherein the microcapsules have a particle size of between 200 and 500 microns.

25. The microcapsule according to claim 1, wherein the at least one deformable organic constituent has a melting point of between 45° C. and 100° C.

26. The microcapsule according to claim 1, wherein the outer overcoating envelope comprises from 5 to 50% of the total dry weight of the microcapsules.

27. The microcapsule according to claim 1, wherein the outer overcoating envelope comprises from 10 to 30% of the total dry weight of the microcapsules.

28. The microcapsule according to claim 1, wherein the outer overcoating envelope comprises in the order of 20% of the total dry weight of the microcapsules.

29. The microcapsule according to claim 1, wherein the at least one film coating comprises at least one film-forming polymer (P1) comprising a water-insoluble cellulose derivative, wherein P1 is insoluble in the tract fluids and present in an amount of 50 to 90% by dry weight, based on the total weight of the coating composition, and wherein the at least one film coating further comprises at least one nitrogen-containing polymer (P2) comprising polyacrylamide, poly-N-vinylamide, poly-N-vinyllactam, or mixtures thereof, wherein P2 is present in an amount of 2 to 25% by dry weight, based on the total weight of the coating composition; at least one plasticizer comprising a glycerol ester, a phthalate, a citrate, a sebacate, a cetyl alcohol ester, castor oil, salicylic acid, cutin, or mixtures thereof, wherein the plasticizer is present in an amount of 2 to 20% by dry weight, based on the total weight of the coating composition; and at least one anionic surfactant, non-ionic surfactant, lubricant, or mixtures thereof present in an amount of 2 to 20% by dry weight, based on the total weight of the coating composition.

* * * * *